United States Patent
Shobako et al.

(10) Patent No.: US 10,676,505 B2
(45) Date of Patent: Jun. 9, 2020

(54) TRIPEPTIDES HAVING ANGIOTENSIN CONVERTING ENZYME INHIBITORY ACTIVITY AND USES THEREOF

(71) Applicant: SUNSTAR INC., Osaka (JP)

(72) Inventors: Naohisa Shobako, Osaka (JP); Kousaku Ohinata, Kyoto (JP); Yuutarou Ogawa, Osaka (JP); Etsuko Kobayashi, Osaka (JP); Atsushi Ishikado, Osaka (JP); Hirohisa Suidou, Osaka (JP); Takashi Kusakari, Osaka (JP)

(73) Assignee: SUNSTAR INC., Osaka (JP)

( * ) Notice: Subject to any disclaimer, the term of this patent is extended or adjusted under 35 U.S.C. 154(b) by 0 days.

(21) Appl. No.: 16/309,641

(22) PCT Filed: Jun. 16, 2017

(86) PCT No.: PCT/JP2017/022340
§ 371 (c)(1),
(2) Date: Jan. 24, 2019

(87) PCT Pub. No.: WO2017/217535
PCT Pub. Date: Dec. 21, 2017

(65) Prior Publication Data
US 2019/0233472 A1    Aug. 1, 2019

(30) Foreign Application Priority Data

Jun. 16, 2016 (JP) .............................. 2016-119853

(51) Int. Cl.
| | | |
|---|---|---|
| *A61K 38/06* | (2006.01) | |
| *A61K 38/00* | (2006.01) | |
| *A61K 38/55* | (2006.01) | |
| *C07K 5/08* | (2006.01) | |
| *A61P 9/12* | (2006.01) | |
| *A23L 33/17* | (2016.01) | |
| *C07K 5/083* | (2006.01) | |
| *A61K 9/00* | (2006.01) | |

(52) U.S. Cl.
CPC ............ *C07K 5/0808* (2013.01); *A23L 33/17* (2016.08); *A61K 9/0053* (2013.01); *A61K 38/06* (2013.01); *A61K 38/55* (2013.01); *A61P 9/12* (2018.01); *A61K 38/00* (2013.01)

(58) Field of Classification Search
CPC ........ A61K 38/00; A61K 38/06; A61K 38/55; A61K 9/0053; C07K 5/0808; C07K 5/08; C07K 5/0802; C07K 5/0806; A61P 9/12; A23L 33/17
USPC ......................................... 514/21.9; 530/331
See application file for complete search history.

(56) References Cited

U.S. PATENT DOCUMENTS

| | | |
|---|---|---|
| 2011/0008891 A1 | 1/2011 | Nakajima et al. |
| 2013/0345396 A1 | 12/2013 | Nakahara et al. |
| 2016/0008459 A1 | 1/2016 | Shirakawa et al. |
| 2016/0145605 A1 | 5/2016 | Kadonosono et al. |

FOREIGN PATENT DOCUMENTS

| | | | |
|---|---|---|---|
| JP | 4-264096 | 9/1992 | |
| JP | 6-166697 | 6/1994 | |
| JP | 7-215889 | 8/1995 | |
| JP | 2004-99552 | 4/2004 | |
| JP | 2005-220091 | 8/2005 | |
| JP | 2006-520809 | 9/2006 | |
| JP | 2010-138133 | 6/2010 | |
| JP | 2010-163400 | 7/2010 | |
| WO | 2004/082709 | 9/2004 | |
| WO | WO-2006108211 A1 * | 10/2006 | ........... C07K 5/0806 |
| WO | 2009/116639 | 9/2009 | |
| WO | 2014/129412 | 8/2014 | |
| WO | 2014/175305 | 10/2014 | |

OTHER PUBLICATIONS

Shobako et al, "A Novel Antihypertensive Peptide Identified in Thermolysin-Digested Rice Bran," Molecular Nutrition and Food Research, 62: 1-7. (Year: 2017).*

Shobako et al, "A Novel Antihypertensive Peptide Identified in Thermolysin-Digested Rice Bran," Molecular Nutrition and Food Research, (evidence that the first publication date is Dec. 27, 2017), p. 1. (Year: 2017).*

International Search Report dated Sep. 19, 2017 in International (PCT) Application No. PCT/JP2017/022340.

Clark et al., "Pervasive adaptive evolution in primate seminal proteins", PLoS Genet., vol. 1, No. 3, E35, 2005, GenBank: AAZ82279.1, https://www.ncbi.nlm.nih.gov/protein/AAZ82279.

* cited by examiner

*Primary Examiner* — Julie Ha
(74) *Attorney, Agent, or Firm* — Wenderoth, Lind & Ponack, L.L.P.

(57) ABSTRACT

Provided is a novel peptide having ACE inhibitory activity. Specifically, provided is a tripeptide consisting of Leu-Arg-Ala.

6 Claims, 2 Drawing Sheets

TRIPEPTIDES HAVING ANGIOTENSIN CONVERTING ENZYME INHIBITORY ACTIVITY AND USES THEREOF

TECHNICAL FIELD

The present invention relates to a novel tripeptide, and an ACE-inhibiting composition, a blood pressure-lowering composition, and the like that comprise the tripeptide.

BACKGROUND ART

Angiotensin-converting enzyme (angiotensin I-converting enzyme; also referred to as "ACE" in the present specification) is an enzyme that converts angiotensin I into angiotensin II. Angiotensin II has the action of increasing blood pressure by, for example, contracting blood vessels. It is known that when the action of ACE is inhibited, the production of angiotensin II is suppressed, thereby showing an anti-hypertensive effect. Accordingly, ACE-inhibitory substances are used, for example, as active ingredients of blood pressure-lowering agents, and food-related components suitable for people with elevated blood pressure.

As the number of patients with hypertension and people with elevated blood pressure has recently been increasing, demand has grown for substances that are safe and have excellent ACE inhibitory activity, and research and development of such substances have been actively conducted. One example of such research and development is the search for peptides that have ACE inhibitory activity. For example, PTL 1 reports that 3 tripeptides having blood pressure-lowering action by ACE inhibition were discovered from a thermolysin digestion product of sesame, PTL 2 reports that a peptide having ACE inhibitory activity was discovered from a digestion product of pig-derived protein with pepsin, PTL 3 reports that a peptide having ACE inhibitory activity was discovered from an enzymatic digestion product of fish-derived protein, PTL 4 reports that a peptide having sequences of decomposed fragments of angiotensin II has ACE inhibitory activity, and PTL 5 reports a dipeptide having ACE inhibitory activity.

CITATION LIST

Patent Literature

PTL 1: JP2006-520809A
PTL 2: JP2005-220091A
PTL 3: JPH06-166697A
PTL 4: JPH07-215889A
PTL 5: JP2004-099552A

SUMMARY OF INVENTION

Technical Problem

The present invention was made in consideration of the actual circumstances of the above prior art. An object of the present invention is to provide a novel peptide having ACE inhibitory activity.

Solution to Problem

As a result of intensive study to achieve the above object, the present inventors found that a tripeptide consisting of Leu-Arg-Ala has excellent ACE inhibitory activity. The present inventors have completed the present invention upon further study based on this finding.

The present invention typically includes inventions described in the following items.

Item 1. A tripeptide consisting of Leu-Arg-Ala.

Item 2. An ACE-inhibiting composition comprising a tripeptide consisting of Leu-Arg-Ala.

Item 3. A blood pressure-lowering composition comprising a tripeptide consisting of Leu-Arg-Ala.

Item 4. The composition according to Item 2 or 3, which is a food composition or a pharmaceutical composition.

Item 5. The composition according to any one of Items 2 to 4, which is an oral composition.

Item 6. The composition according to any one of Items 2 to 5, which is used so that the tripeptide consisting of Leu-Arg-Ala is taken in an amount of 10 to 300 µg by an adult per day.

Item 7. The composition according to any one of Items 2 to 6, which is used so that the composition is taken for 9 to 12 weeks or longer.

Item A-1. A method for inhibiting ACE or lowering blood pressure, the method comprising administering a tripeptide consisting of Leu-Arg-Ala, or a composition comprising the polypeptide and a pharmaceutically or hygienically acceptable carrier, to a subject.

Item B-1. A tripeptide consisting of Leu-Arg-Ala, or a composition comprising the polypeptide and a pharmaceutically or hygienically acceptable carrier, for use in suppressing hypertension.

Item C-1. Use of a tripeptide consisting of Leu-Arg-Ala in the production of medicines or food for suppressing hypertension.

Advantageous Effects of Invention

Since the tripeptide consisting of Leu-Arg-Ala of the present invention has excellent ACE inhibitory activity and blood pressure-lowering effect, the intake or administration of the tripeptide consisting of Leu-Arg-Ala results in an ACE-inhibiting effect and a blood pressure-lowering effect.

BRIEF DESCRIPTION OF DRAWINGS

In FIG. 2, "Control" shows the results of a control group, and "LRA 0.25 mg/kg" shows the results of an LRA peptide administration group. An asterisk ("*") indicates that there was a significant difference ($p<0.05$) relative to the control group.

DESCRIPTION OF EMBODIMENTS

Figure 1:
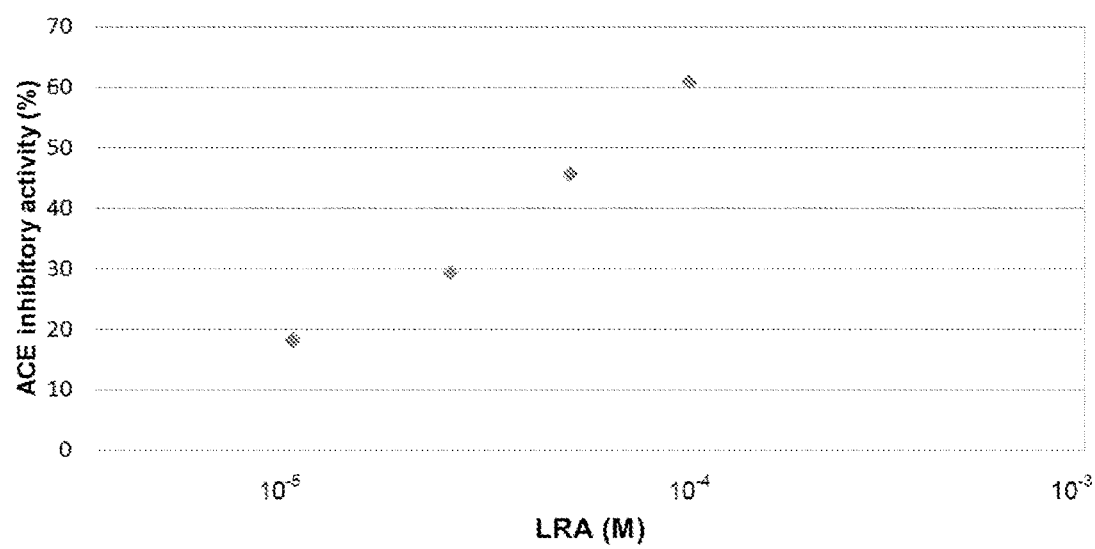
FIG. 1 is a graph showing the results of ACE inhibitory activity ($IC_{50}$ value) measured in Example 1.

The present invention is described in detail below. In the present specification, the ACE-inhibiting composition and blood pressure-lowering composition of the present invention are also generically referred to as "the composition of the present invention."

The present invention includes a tripeptide consisting of an amino acid sequence: Leu-Arg-Ala (also referred to as the "LRA peptide" in the present specification).

The LRA peptide can be prepared by chemical synthesis by using a known peptide synthesis method. Examples of peptide synthesis methods include azide methods, acid chloride methods, acid anhydride methods, mixed acid anhydride methods, DDC methods, active ester methods, carboimidazole methods, oxidation reduction methods, and other peptide synthesis methods. These peptide synthesis methods can be performed by a solid-phase synthesis method or a liquid-phase synthesis method.

In the above peptide synthesis methods, amino groups, carboxy groups, and/or side-chain functional groups (e.g., the guanidino group of arginine (Arg)) are preferably protected with protecting groups. The protecting groups are not limited, and known protecting groups can be used. Examples include a benzyloxycarbonyl group (Cbz), a tert-butoxycarbonyl group (Boc), a fluorenyl methoxycarbonyl group (Fmoc), a benzyl group (Bz), a p-toluenesulfonyl group (p-Ts), and the like.

Further, the LRA peptide used herein can be one obtained by synthesizing an LRA peptide by the above peptide synthesis method, optionally followed by purification by a known method.

The LRA peptide has ACE inhibitory activity and blood pressure-lowering action, and thus can be used as an ACE activity-inhibiting composition, a blood pressure-lowering composition, a blood pressure elevation-inhibiting composition, an antihypertensive composition, or the like. Moreover, the composition of the present invention can be preferably used as an oral composition, such as a pharmaceutical composition or a food composition.

In the present specification, the food composition includes not only food compositions, but also compositions that are widely taken as food or drink, such as salt substitutes, sweeteners, additives for beverages, and other food additive compositions; and premixed food products for commercial or home use, and other food material compositions. In particular, when the composition of the present invention is used as a food composition, it can be preferably used as a food composition with product display clearly showing its action, effect, etc., for blood pressure. Specific examples include food compositions with product display clearly showing their action and effects, such as preventing hypertension, suppressing blood pressure elevation, and lowering blood pressure; and include food compositions with product display clearly showing that they are for people with elevated blood pressure, people who are concerned about their blood pressure, etc.

When the composition of the present invention is used as a pharmaceutical composition, it can contain other components, if necessary, in addition to the LRA peptide. The other components are not limited, and can be suitably selected depending on the purpose. Examples include pharmaceutically acceptable bases, carriers, and/or additives (e.g., solvents, dispersants, emulsifiers, buffers, stabilizers, excipients, binders, disintegrators, and lubricants). The amounts of the other components can be suitably determined depending on the purpose.

When the composition of the present invention is used as a pharmaceutical composition, the administration route thereof is not limited. Examples include oral administration, intravenous injection, and the like. Of these, oral administration is preferable.

When the composition of the present invention is used as a pharmaceutical composition, the dosage form thereof is not limited. Examples include tablets, such as orally disintegrating tablets, chewable tablets, foaming tablets, dispersing tablets, and soluble tablets; troches; powders; suspensions; emulsions; elixirs; limonades; syrups; lotions; granules; capsules, such as hard capsules and soft capsules; creams; ointments; suppositories; transdermal/mucosal administration agents, such as cataplasms, tapes, microneedles, iontophoresis, and electroporation; aerosols; and the like. These forms can be prepared by combining the LRA peptide and the other components described above, if necessary, using a general method.

When the composition of the present invention is used as a pharmaceutical composition or a quasi-drug, the amount of the LRA peptide in the pharmaceutical composition is not limited as long as it is an amount that allows the LRA peptide to exhibit its ACE inhibitory activity and blood pressure-lowering action. The amount of the LRA peptide can be suitably determined.

Moreover, when the composition of the present invention is used as a pharmaceutical composition, the dose, dosing interval, administration subject, etc., are not limited, and can be suitably determined. For example, the dose can be suitably determined depending on the age, sex, and body weight of the administration subject, the health conditions of the subject, and other conditions. Further, the dosing interval may be, for example, once or several times (preferably 2 or 3 times) per day, or once or several times per several days to several weeks. The administration subject may be a human or a nonhuman mammal, such as pets or livestock.

In particular, when the administrated subject is a human, the amount of LRA peptide administered to (taken by) an adult per day is, for example, preferably about 10 to 300 μg, more preferably about 15 to 200 μg, even more preferably about 20 to 100 μg, still more preferably about 30 to 80 μg, further still more preferably about 35 to 70 μg, and particularly preferably about 40 to 60 μg.

Moreover, the administration (intake) period is not limited, but is preferably 3 to 12 weeks or longer (3, 4, 5, 6, 7, 8, 9, 10, 11, or 12 weeks or longer), and more preferably 9 to 12 weeks or longer. In particular, when the amount of LRA peptide administered per day is about 30 to 80 μg, the administration period is preferably 5 to 12 weeks or longer. When the amount of LRA peptide administered per day is 10 μg or more and less than 30 μg, or more than 80 μg and 300 μg or less, the administration period is preferably 9 to 12 weeks or longer.

When the administration subject is a nonhuman mammal, the administration route, dosage form, dose, dosing interval, etc., can be suitably determined with reference to a case in which the administration subject is a human.

When the composition of the present invention is used as a food composition, it can contain other components, if necessary, in addition to the LRA peptide. The other components are not limited, and can be suitably selected depending on the purpose. Examples include hygienically acceptable bases, carriers, and additives, as well as components, materials, etc., that can be used as food.

When the composition of the present invention is used as a food composition, the intake route is oral ingestion. In this case, the form of the composition of the present invention is not limited, and the composition of the present invention can be used for general food, food with health claims, and food for special dietary uses. Examples include food for specified health use, food with nutrient function claims, functional display food, food for sick people, food for people with dysphagia, health supplements, nutritional supplements, hospital food, care food, processed food, beverages, and the like. These can be prepared by general methods. Examples of the dosage form of food compositions include hard capsules, soft capsules, supplements, chewable tablets, beverages, powder drinks, granules, films, and other forms. In addition, for use as food and drink, examples include beverages, such as tea beverages, sports drinks, cosmetic drinks, fruit juice beverages, carbonated beverages, liquors, soft drinks, jelly drinks, and concentrated beverages diluted with water, hot water, carbonated water, etc.; powder and granules that are drunk after being dissolved or suspended in water, hot water, etc.; dry solid forms, such as tablets; confectionery, such as tablet confectionery, jellies, snacks, baked goods, fried cakes, cakes, chocolate, gum, candies, and gummy candies; soup, noodles, rice, cereal, and other food forms. Among these, preferable forms for ordinary life include supplements, chewable tablets, one-shot drinks, etc.; and forms preferable for intake for the purpose of enhancing exercise effects include beverages, such as sports drinks. In particular, when the composition of the present invention is used as food with health claims, a health supplement, a nutritional supplement, etc., examples of preferable forms, in order to facilitate continuous intake, include granules, capsules, tablets and pills (including chewable agents etc.), beverages (including drink powder, health drink, etc.), jellies, and the like.

Moreover, when the composition of the present invention is used as a food additive composition or a food material composition, the form thereof is not limited. Examples include liquid, powder, flakes, granules, and pastes. Specific examples include seasonings (sweeteners, salt substitute compositions, soy sauce, vinegar, miso, sauce, ketchup, dressings, spices, herbs, etc.), flakes (furikake (topping for rice), rice additives, etc.), barbecue sauce, roux paste (e.g., curry roux paste), premixed food products, and the like.

When the composition of the present invention is used as a food composition, the amount of the LRA peptide in the food composition is not limited as long as it is an amount that allows the LRA peptide to exhibit its ACE inhibitory activity, blood pressure-lowering action, and blood pressure elevation inhibitory action. The amount of the LRA peptide can be suitably determined.

Moreover, when the composition of the present invention is used as a food composition, the intake amount, intake interval, intake subject, etc., are not limited, and can be suitably determined. For example, the intake amount can be suitably determined depending on the age, sex, and body weight of the intake subject, the health conditions of the subject, and other conditions. For example, when the above amount is taken, the intake interval may be once or several times (preferably 2 or 3 times) per day, or once or several times per several days to several weeks. Moreover, the intake subject may be a human or a nonhuman mammal, such as pets or livestock.

In particular, when the intake subject is for a human, the amount of LRA peptide taken by an adult per day is preferably about 10 to 300 µg, more preferably about 15 to 200 µg, even more preferably about 20 to 100 µg, still more preferably about 30 to 80 µg, further sill more preferably about 35 to 70 µg, and particularly preferably about 40 to 60 µg.

The intake period is not limited, but is preferably 3 to 12 weeks or longer (3, 4, 5, 6, 7, 8, 9, 10, 11, or 12 weeks or longer), and more preferably 9 to 12 weeks or longer. In particular, when the amount of LRA peptide taken per day is about 30 to 80 µg, the intake period is preferably 5 to 12 weeks or longer. When the amount of LRA peptide taken per day is 10 µg or more and less than 30 µg, or more than 80 µg and 300 µg or less, the intake period is preferably 9 to 12 weeks or longer.

The people qualified as intake subjects are not limited. Preferable subjects are people who want to prevent elevated blood pressure associated with aging, and people who need to prevent elevated blood pressure or to lower blood pressure. Specifically, preferable subjects are not only people classified as having hypertension (systolic blood pressure of 140 mmHg or more and/or diastolic blood pressure of 90 mmHg or more) according to the Guidelines for Hypertension Treatment 2014, published by the Japanese Society of Hypertension, but also people who are classified as having normal blood pressure (systolic blood pressure of 120 to 129 mmHg and/or diastolic blood pressure of 80 to 84 mmHg) or high-normal blood pressure (systolic blood pressure of 130 to 139 mmHg and/or diastolic blood pressure of 85 to 89 mmHg) but revealed to be highly likely to develop hypertension during their lifetime. Among these, people classified as having normal high blood pressure or hypertension are more preferable, and people classified as having normal high blood pressure are even more preferable.

When the intake subject is a nonhuman mammal, the form, intake amount, intake interval, etc., can be suitably determined with reference to a case in which the intake subject is a human.

EXAMPLES

The present invention is described in more detail below with reference to Examples; however, the present invention is not limited to the following Examples.

Production Example 1

Synthesis of Tripeptide by Fmoc Method

A tripeptide consisting of Leu-Arg-Ala was solid-phase synthesized by the Fmoc method. After the obtained LRA peptide was purified by HPLC, the sequence was analyzed with a protein sequencer. As a result, it was confirmed that this tripeptide was a tripeptide consisting of Leu-Arg-Ala.

Production Example 2

Synthesis of Tripeptide by Boc Method

Synthesis of a tripeptide consisting of Leu-Arg-Ala by the Boc method was requested of Peptide Institute, Inc. RP-HPLC, mass analysis, and amino acid analysis confirmed that the delivered LRA peptide was a tripeptide consisting of Leu-Arg-Ala.

Example 1

Measurement of ACE Inhibitory Activity

Ultrapure water was added to the LRA peptide synthesized in Production Example 1 to prepare a 300 µM aqueous solution. Subsequently, 300-µM, 150-µM, 75-µM, and 30-µM aqueous solutions were each prepared by gradual dilution. These aqueous solutions were used as samples.

The ACE inhibitory activity of each sample was measured using an ACE inhibitory activity measurement kit (trade name: ACE Kit-WST, produced by Dojindo Laboratories). The kit is used to detect 3-hydroxybutyric acid (3HB) cut from 3-hydroxybutyryl-Gly-Gly-Gly (3HB-GGG) by an enzyme method. The operation was carried out according to the instruction manual of the kit, and the ACE inhibitory activity of each sample was measured (N=3). In the kit, the final concentration of the LRA peptide in each sample drops to ⅓. FIG. 1 shows the results. Further, the $IC_{50}$ value of the LRA peptide calculated from the measurement results was 62 μM.

The above results demonstrated that the LRA peptide had excellent ACE inhibitory activity.

Example 2

Examination of Blood Pressure-Lowering Action

Male spontaneously hypertensive rats (SHR/Izm, 12 weeks old) were used as experimental animals. The feed used was solid SP feed (Funabashi Farm), and the drinking water used was tap water. Food intake and drinking water were unrestricted, including during the test. The rats after a habituation period of three weeks were used for the main test. The rats were divided into two groups: an LRA peptide administration group and a control group (each group: N=5).

Figure 2:
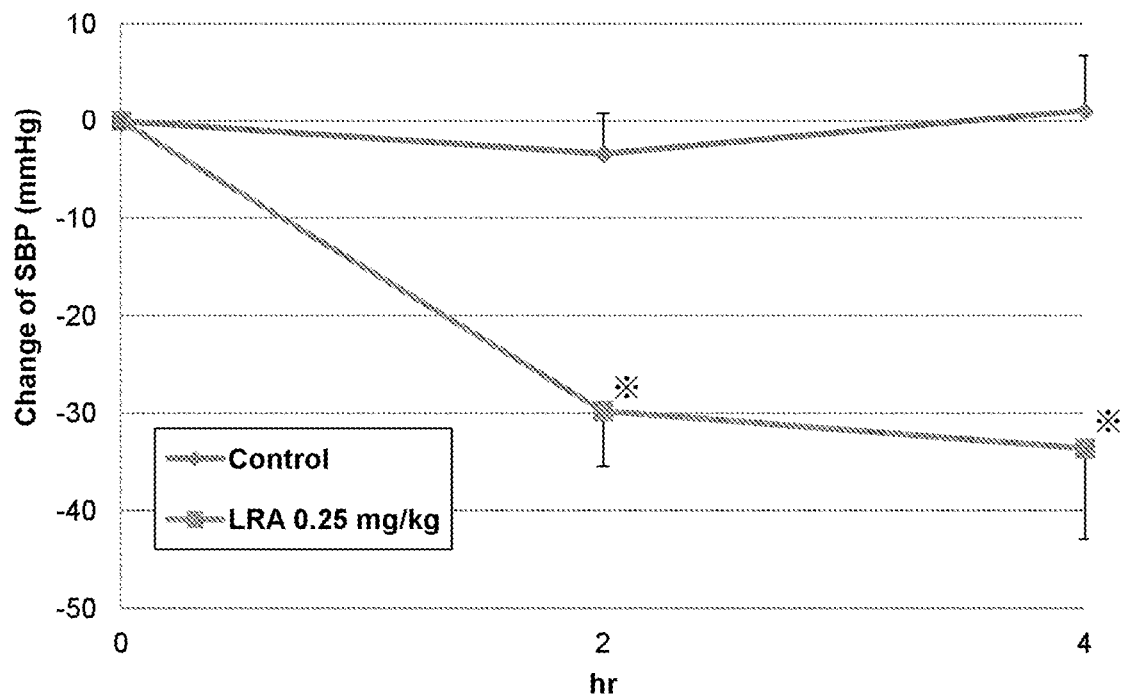
FIG. 2 is a graph showing the results of a test for examining blood pressure-lowering action performed in Example 2.

The LRA peptide synthesized in Production Example 2 was dissolved in physiological saline to prepare a 0.25-mg/ml peptide solution. In the LRA peptide administration group, 0.25 mg/kg of the peptide solution was forcibly administered orally into the stomach by using a 1-ml-volume syringe and a Teflon (registered trademark) stomach tube. In the control group, physiological saline was forcibly orally administered in the same manner as in the sample administration group. Systolic blood pressure was measured by the tail-cuff method before administration, and 2 hours and 4 hours after administration. In the measurement of blood pressure, a blood pressure monitor (MK-2000ST, produced by Muromachi Kikai Co., Ltd.) was used. The degree of reduction in the systolic blood pressure 2 hours and 4 hours after administration compared with the systolic blood pressure before administration was used as an indicator. FIG. 2 shows the results.

It was revealed that, compared with the control group, the LRA peptide administration group showed a significant reduction in systolic blood pressure 2 hours and 4 hours after administration. The results demonstrated that the LRA peptide had excellent blood pressure-lowering action.

Example 3

Human Clinical Test

The blood pressure-lowering effect of the LRA peptide was examined by placebo-controlled double-blind randomized intergroup trial.

Tablets containing 0 g, 3 μg, 6 μg, or 12 μg of the LRA peptide were prepared using food carriers (dietary fiber etc.). Examples of the component analysis results of these tablets were as follows: water: 7.9 g/100 g (measured by a normal pressure heating-drying method); lipid: 0.3 g/100 g (measured by the acid decomposition method); ash content: 26.4 g/100 g (measured by the direct ashing method); sodium: 757 mg/100 g (measured by atomic absorption spectrophotometry; sodium chloride equivalent: 1.92 g/100 g).

Figure 3:
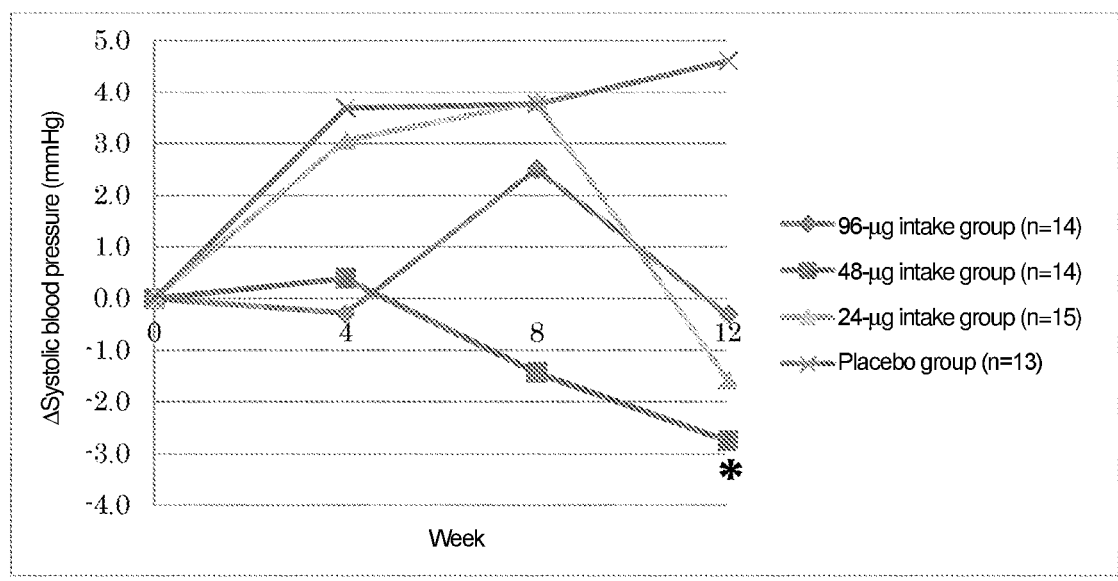
FIG. 3 shows the results of a human clinical test that examined the blood pressure-lowering effect of the LRA peptide by placebo-controlled double-blind randomized trial. An asterisk ("*") indicates that there was a significant difference ($p<0.05$, t-test) in comparison with the placebo group.

A total of 80 subjects, including men and women aged 35 or more and less than 65 who had normal high blood pressure (systole of 130 to 139 mmHg or diastole of 85 to 89 mmHg) or stage 1 hypertension (systole of 140 to 159 mmHg or diastole of 90 to 99 mmHg), were divided into four groups: a placebo group, a 24-μg intake group, a 48-μg intake group, and a 96-μg intake group (20 people in each group). In the placebo group, 8 tablets not containing the LRA peptide were taken per day. In the 24-μg intake group, 8 tablets containing 3 μg of the LRA peptide (total amount of the LRA peptide: 24 μg) were taken per day. In the 48-μg intake group, 8 tablets containing 6 μg of the LRA peptide (total amount of the LRA peptide: 48 μg) were taken per day. In the 96-μg intake group, 8 tablets containing 12 μg of the LRA peptide (total amount of the LRA peptide: 96 μg) were taken per day. Each subject took 8 tablets per day over 12 weeks. Then, the blood pressure of each subject was measured immediately before the start of intake, 4 weeks after the start of intake, 8 weeks after the start of intake, and 12 weeks after the start of intake. An automatic blood pressure monitor (HEM-759P, produced by Omron Corporation) was used for the measurement. Measurements were performed twice, and their average value was recorded as the blood pressure of each subject. For the subjects aged 45 or more with a BMI of less than 30, FIG. 3 is a graph showing differences between systolic blood pressure values immediately before the start of intake, and systolic blood pressure values 4 weeks after the start of intake, 8 weeks after the start of intake, and 12 weeks after the start of intake. In FIG. 3, an asterisk ("*") indicates that there was a significant difference ($p<0.05$, t-test) in comparison with the placebo group.

The invention claimed is:

1. A method for inhibiting angiotensin-converting enzyme activity, comprising administering to a subject in need thereof an effective amount of a tripeptide consisting of Leu-Arg-Ala.

2. The method according to claim 1, comprising administering to an adult the tripeptide in an amount of 10 to 300 μg per day.

3. The method according to claim 1, comprising administering to a subject the tripeptide for 9 to 12 weeks or longer.

4. A method for lowering blood pressure, comprising administering to a subject in need thereof an effective amount of the tripeptide consisting of Leu-Arg-Ala.

5. The method according to claim 4, comprising administering to an adult the tripeptide in an amount of 10 to 300 μg per day.

6. The method according to claim 4 comprising administering to the subject the tripeptide for 9 to 12 weeks or longer.

* * * * *